United States Patent
Ayers et al.

(10) Patent No.: US 11,013,418 B2
(45) Date of Patent: May 25, 2021

(54) IDENTIFICATION OF DEVICE LOCATION IN HEALTHCARE FACILITY

(71) Applicant: Hill-Rom Services, Inc., Batesville, IN (US)

(72) Inventors: Brandon Ayers, Batesville, IN (US); Collin Davidson, Apex, NC (US); Stephen Embree, Chapel Hill, NC (US); Kenzi L. Mudge, Raleigh, NC (US); Britten Pipher, Raleigh, NC (US); Timothy Receveur, Apex, NC (US); Mickael Audic, Locmiquelic (FR); Jean-Bernard Duvert, Auray (FR); Alonso De La Vega Gomez, Lorient (FR); Philippe Kaikenger, Pluvigner (FR)

(73) Assignee: HILL-ROM SERVICES, INC., Batesville, IN (US)

( * ) Notice: Subject to any disclaimer, the term of this patent is extended or adjusted under 35 U.S.C. 154(b) by 0 days.

(21) Appl. No.: 16/784,405

(22) Filed: Feb. 7, 2020

(65) Prior Publication Data
US 2020/0170516 A1 Jun. 4, 2020

Related U.S. Application Data

(63) Continuation-in-part of application No. 16/669,856, filed on Oct. 31, 2019.
(Continued)

(51) Int. Cl.
*H04B 5/00* (2006.01)
*H04W 4/80* (2018.01)
(Continued)

(52) U.S. Cl.
CPC .......... *A61B 5/0205* (2013.01); *A61B 5/6892* (2013.01); *G06F 3/04886* (2013.01);
(Continued)

(58) Field of Classification Search
CPC .. H04B 5/0056; H04B 5/0025; H04B 5/0043; H04B 5/0062; H04W 4/80; H04W 4/02;
(Continued)

(56) References Cited

U.S. PATENT DOCUMENTS 7,268,294 B2 9/2007 Ohkawa et al.
7,399,205 B2 7/2008 McNeely et al.
(Continued)

OTHER PUBLICATIONS

European Search Report, Application No. EP 19 20 6752, dated Mar. 26, 2020, 9 pages.

*Primary Examiner* — Andrew Wendell
(74) *Attorney, Agent, or Firm* — Merchant & Gould P.C.

(57) ABSTRACT

A system for identifying a location of a device includes a first antenna mounted to a plug. The first antenna surrounds one or more prongs of the plug, and the plug has a memory that stores a device ID. A second antenna receives the device ID from the first antenna when the plug is coupled to a power outlet. A controller uses a communication module to wirelessly transfer the device ID and a power outlet ID to a computer server. The computer server uses the device ID and the power outlet ID to determine the location of the device within a building.

17 Claims, 12 Drawing Sheets

Related U.S. Application Data

(60) Provisional application No. 62/754,157, filed on Nov. 1, 2018.

(51) Int. Cl.
```
A61B 5/0205      (2006.01)
G06F 3/0488      (2013.01)
H04W 76/11       (2018.01)
A61B 5/00        (2006.01)
H01R 31/06       (2006.01)
A61B 5/024       (2006.01)
G16H 10/60       (2018.01)
A61B 5/11        (2006.01)
A61B 5/103       (2006.01)
A61B 5/08        (2006.01)
```

(52) U.S. Cl.
CPC .......... *H01R 31/065* (2013.01); *H04W 76/11* (2018.02); *A61B 5/02438* (2013.01); *A61B 5/0816* (2013.01); *A61B 5/1036* (2013.01); *A61B 5/1113* (2013.01); *A61B 2560/0475* (2013.01); *A61B 2562/226* (2013.01); *A61B 2562/227* (2013.01); *G16H 10/60* (2018.01)

(58) Field of Classification Search
CPC .......... H04W 4/029; H04W 12/00503; H04W 12/00407; H01Q 1/36; H01R 13/719; H01R 31/065; H01R 13/465; H01R 13/6691; H01R 24/76; H01R 13/665
See application file for complete search history.

(56) References Cited

U.S. PATENT DOCUMENTS

| | | |
|---|---|---|
| 7,483,797 B2 | 1/2009 | Nambu |
| 8,610,562 B2 | 12/2013 | Weiner et al. |
| 8,674,826 B2 | 3/2014 | Becker et al. |
| 8,930,158 B2 | 1/2015 | Elberbaum |
| 9,466,877 B2 | 10/2016 | Dixon et al. |
| 9,520,043 B1 | 12/2016 | Alshinnawi |
| 9,830,424 B2 | 11/2017 | Dixon et al. |
| 9,838,836 B2 | 12/2017 | Hayes et al. |
| 9,941,647 B2 | 4/2018 | Huang et al. |
| 10,085,905 B2 | 10/2018 | Bhimavarapu et al. |
| 10,505,326 B2* | 12/2019 | Chien .................... H01R 13/70 |
| 2007/0271474 A1 | 11/2007 | Kim et al. |
| 2013/0135160 A1 | 5/2013 | Dixon et al. |
| 2015/0081335 A1 | 3/2015 | Allen et al. |
| 2017/0301208 A1* | 10/2017 | Mytelka ............. G08B 21/0469 |
| 2018/0026404 A1* | 1/2018 | Geo .................... H01R 13/7037 |
| | | 439/620.21 |
| 2020/0005002 A1 | 1/2020 | Schmidt |
| 2020/0145057 A1* | 5/2020 | Ayers ....................... H01Q 1/36 |

* cited by examiner

IDENTIFICATION OF DEVICE LOCATION IN HEALTHCARE FACILITY

BACKGROUND

The physical location of a device can be an important piece of information. In the healthcare context, medical devices, such as hospital beds, can include special features both for the comfort and well-being of a patient. Identifying the location of a hospital bed with the healthcare facility can be important, particularly when a patient is in need of attention.

SUMMARY

One aspect relates to a system for identifying a location of a device. The system comprises a first antenna mounted to a plug of the device. The first antenna has a coil shape, and the plug has a memory that stores a device ID. The system comprises a second antenna that receives the device ID from the first antenna when the plug is coupled to a power outlet. The system further comprises a controller that receives the device ID from the second antenna, and that uses a communication module to wirelessly transfer the device ID and a power outlet ID to a computer server. The computer server having a processor and a memory, wherein the memory stores instructions that, when executed by the processor, cause the computer server to use the device ID and the power outlet ID to determine the location of the device within a building.

Another aspect relates to a hospital bed that comprises a power cord having at one end a plug and one or more prongs extending from the plug that are configured to couple the plug to a power outlet. The hospital bed further comprises a first antenna carried by the plug. The first antenna has a shape that surrounds the one or more prongs of the plug. The first antenna is a near-field communication antenna having a memory that stores a device ID transferable to a second antenna when the first antenna is proximate the second antenna, the device ID is usable by a computer server to determine the location of the hospital bed within a building.

Another aspect relates to an adapter for a power outlet. The adapter comprises at least one connector port on a front surface, the connector port is configured to receive a plug to electrically connect a device to the adapter. Electrical couplings on a rear surface are insertable into at least one socket of the power outlet to plug the adapter into the power outlet. An electronic board is configured to receive a device ID from the device when plugged into the connector port and an outlet ID identifying a location of the power outlet. A communication transceiver that transmits the device ID and the outlet ID from the electronic board to a central computing system.

Another aspect relates to a method for determining a location of a device within a facility. The method comprises installing an adapter onto a power outlet; entering a power outlet ID into the adapter, the power outlet ID identifying a location of the power outlet within the facility; and plugging a device into the adapter.

Another aspect relates to a method for automatically saving measured parameters. The method comprises receiving a power outlet ID associated with a power outlet in the facility and a device ID associated with a device plugged into the power outlet, the power outlet ID together with the device ID determining the location of the device in the facility; receiving the measured parameters from the device; associating the measured parameters with the location of the device in the facility; and storing the measured parameters.

The details of one or more techniques are set forth in the accompanying drawings and the description below. Other features, objects, and advantages of these techniques will be apparent from the description, drawings, and claims.

DETAILED DESCRIPTION

The present application is directed to the determination of the physical location of a device connected to a power outlet within a building. In the example embodiments described herein, the device is a medical device, such as a hospital bed or patient monitoring device, positioned within a healthcare facility having multiple floors and rooms making it difficult to locate a particular medical device that may or may not be associated with a patient of the healthcare facility. Although the example embodiments are described in the context of a healthcare facility and a hospital bed, the principles of the present application are applicable to other types of scenarios and devices, such as medical diagnostic devices and patient lift devices, as well.

Examples of systems that can assist in locating medical devices, such as hospital beds, within a healthcare facility are provided in U.S. Pat. Nos. 7,399,205; 9,466,877; and 9,830,424. The entireties of these references are hereby incorporated by reference.

Figure 1:
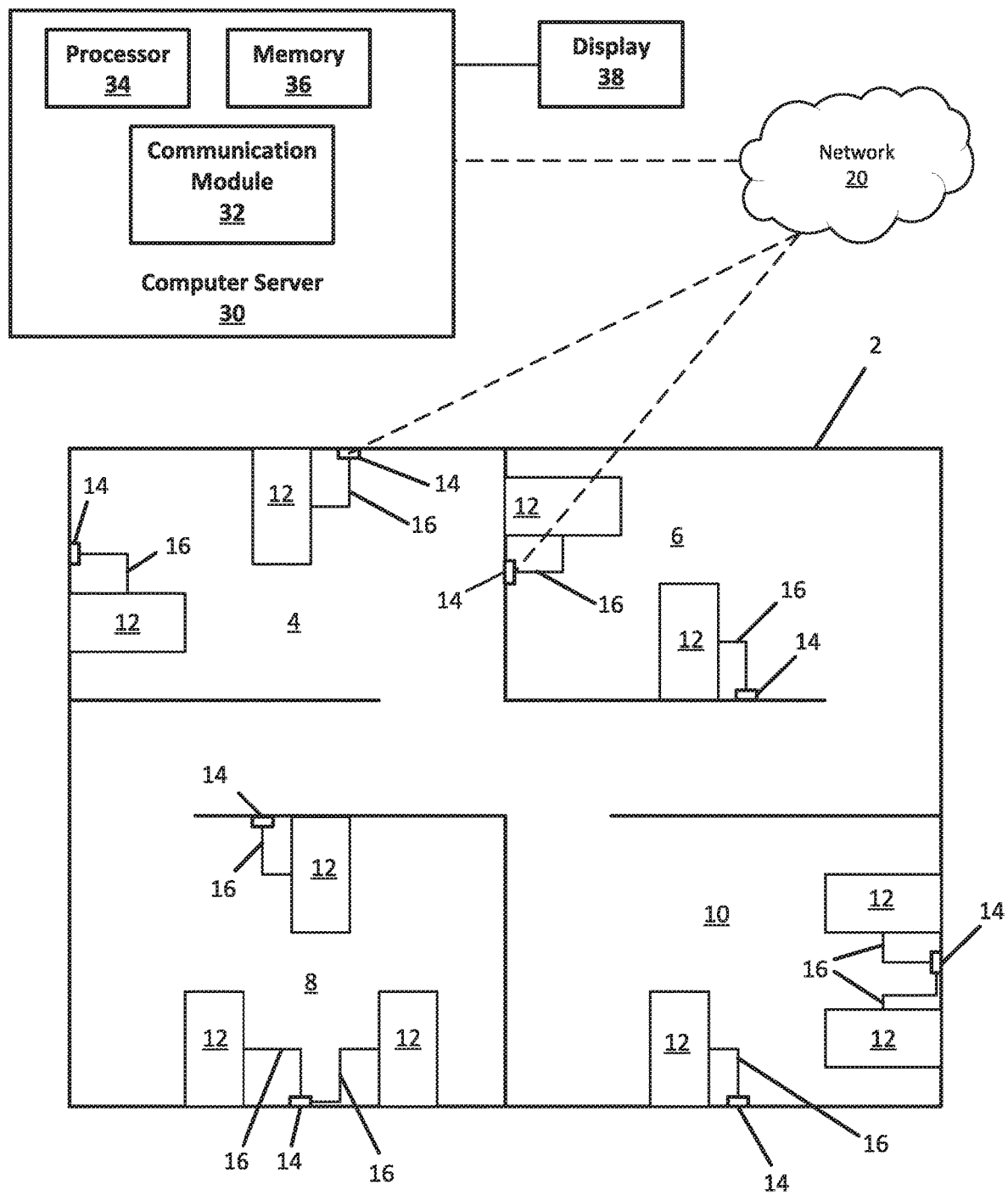
FIG. 1 is a schematic diagram of a healthcare facility having multiple rooms and hospital beds located within each room.

FIG. 1 is a schematic diagram of a healthcare facility 2 having multiple rooms 4, 6, 8, 10 and hospital beds 12 located within each room. Each room within the healthcare facility 2 can have one or more power outlets 14. As shown in FIG. 1, each hospital bed 12 is located next to a power outlet 14 so that a power cord 16 from each hospital bed 12 can be plugged into a power outlet 14 for powering the bed.

As also shown in FIG. 1, each power outlet 14 is connected to a network 20 so that each power outlet 14 can transfer data to the network 20 (only two power outlets 14 are schematically shown connected to the network 20 for ease of illustration). In some examples, each power outlet 14 transfers data wirelessly to the network 20. In other examples, each power outlet 14 transfers data to the network 20 via a wired connection. As will be explained in more detail, the network 20 is connected to a computer server 30 that can use the data transferred from a power outlet 14 to determine a location of a particular hospital bed 12 within the healthcare facility 2.

Figure 2:
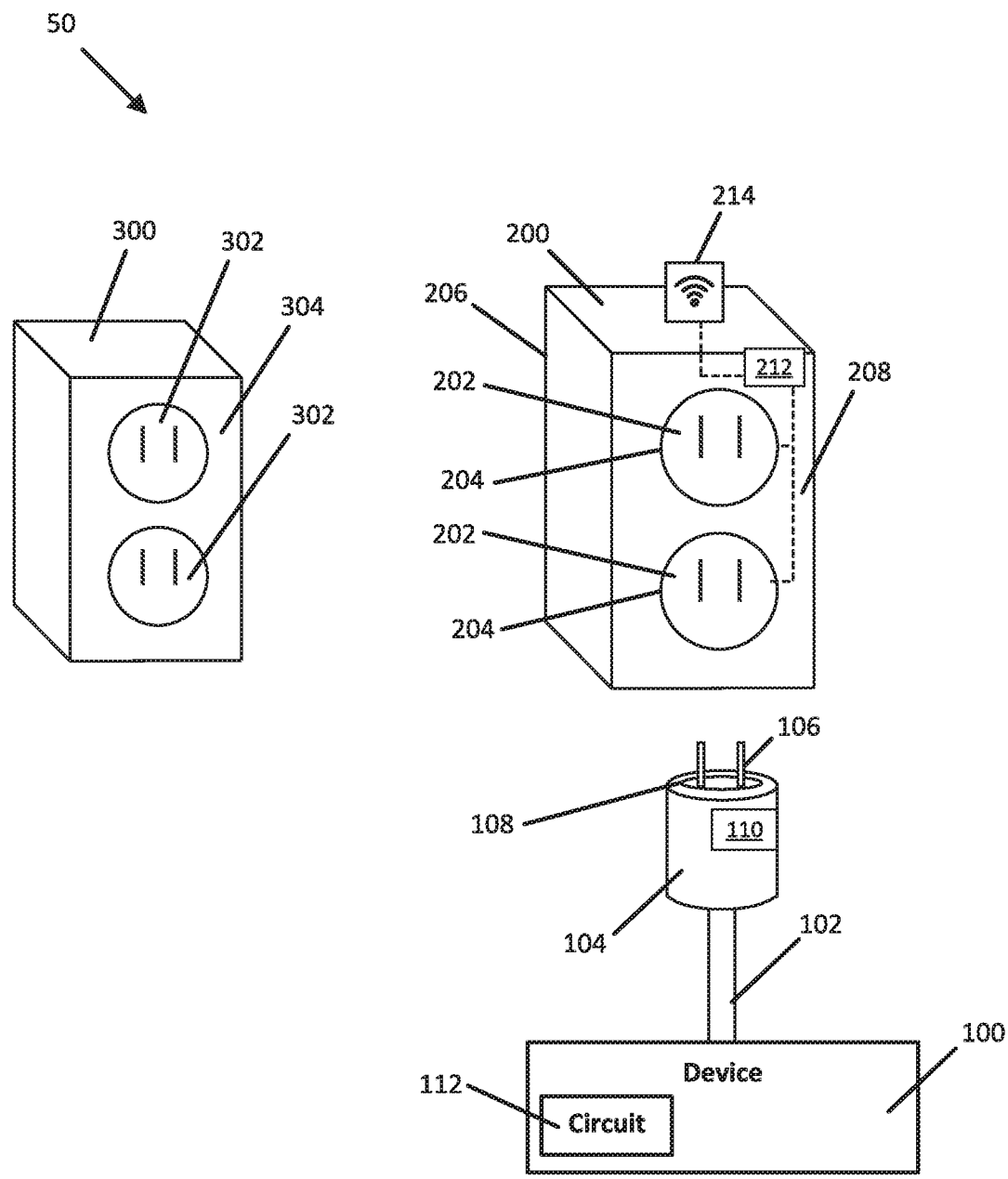
FIG. 2 is schematic diagram of a system that can identify a location of a device.

FIG. 2 is a schematic diagram of a system 50 that can identify a location of a device 100. As shown in FIG. 2, the device 100 includes a power cord 102 having at one end a plug 104 and one or more prongs 106 that extend from the plug 104. The prongs 106 are configured to couple the plug 104 to a socket 302 of a power outlet 300. When coupled to the socket 302, the prongs 106 draw electrical power from the power outlet 300 for powering the device 100. In the example shown, the device 100 is a hospital bed. The prongs 106 draw electrical power from the power outlet 300 for powering the hospital bed, including such features as height adjustment, entertainment options like television control, and/or emergency alert options like a call button that can be actuated by the patient to summon assistance from a caregiver.

In the example shown in FIG. 2, the power outlet 300 has two sockets 302 arranged in a vertical configuration. In other examples, the power outlet 300 can have alternative socket configurations such that the power outlet 300 can have a single socket configuration, or multiple sockets arranged in vertical and/or horizontal configurations.

The plug 104 carries a first antenna 108. The first antenna 108 has a shape that surrounds the one or more prongs 106 of the plug 104. In some examples, the shape of the first antenna 108 is an ellipse (e.g., circle, oval, coil etc.) that surrounds the one or more prongs 106. In other examples, the shape of the first antenna 108 is a rectangle, square, or other shape that can surround the one or more prongs 106. In some alternative examples, it is contemplated that the first antenna 108 can be positioned in other areas of the plug 104.

In some examples, the first antenna 108 is embedded in the plug 104 such that the first antenna 108 is spaced or offset from an exterior surface of the plug 104 in a range from about 3 to about 4 cm. In some examples, the first antenna 108 is embedded in the plug 104 such that the first antenna 108 is spaced or offset from an exterior surface of the plug 104 by less than 3 cm.

The plug 104 can have a memory 110 connected to the first antenna 108 and/or embedded within the first antenna 108. The memory 110 can store data such a device ID that can be used to identify the device 100. In some examples, the memory 110 contains the data as read-only data. In some examples, the data stored on the memory 110 is rewriteable. In some examples, the memory 110 can store other data in addition to the device ID.

Figure 3:
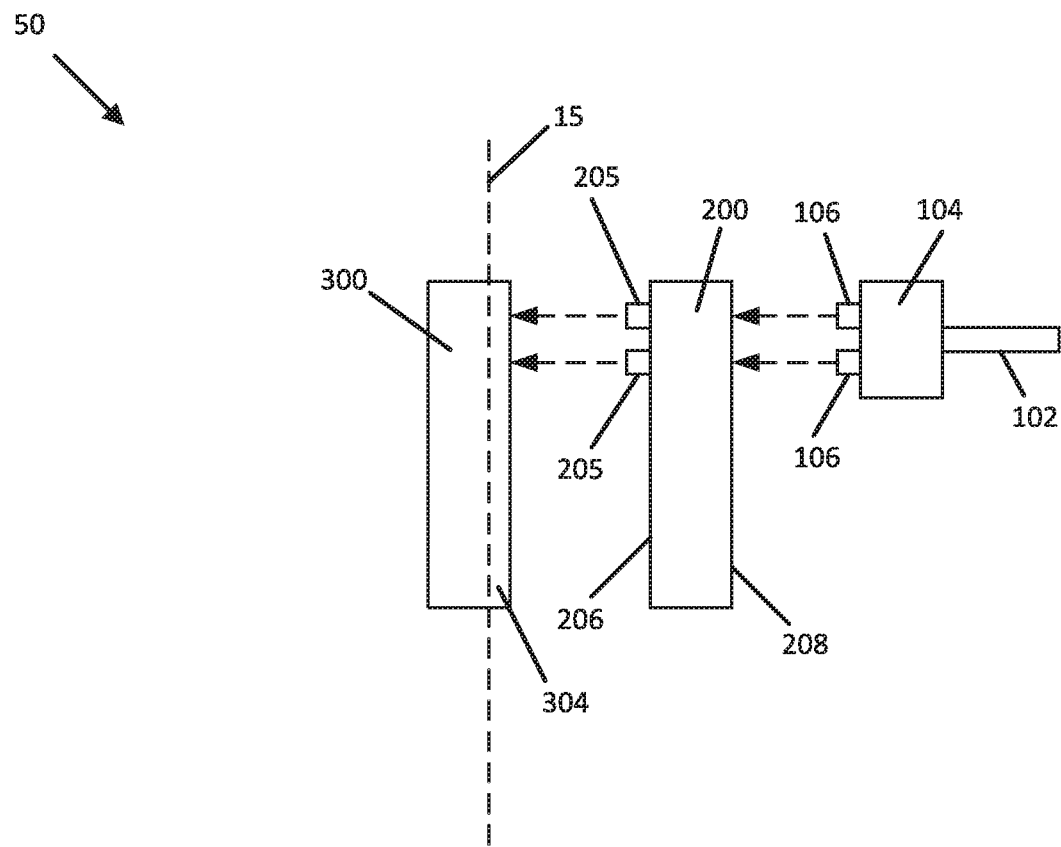
FIG. 3 is a side view showing an interface between a plug, an adapter, and a power outlet in the system of FIG. 2.

In the example shown in FIG. 2, the system 50 includes an adapter 200 that can connect to the power outlet 300. FIG. 3 is a side view showing an interface between the adapter 200 and the power outlet 300. As shown in FIGS. 2 and 3, the adapter 200 can include one or more prongs 205 on a rear surface 206 of the adapter 200 that are insertable into at least one socket 302 in the power outlet 300 to connect the adapter 200 to the power outlet 300. When the adapter 200 is connected to the power outlet 300, the adapter 200 substantially covers a faceplate 304 of the power outlet 300, and is substantially parallel with a wall 15 into which the power outlet 300 is mounted. The adapter 200 has at least one socket 202 on a front surface 208 that can receive the one or more prongs 106 of the plug 104. When connected to the power outlet 300, the adapter 200 can provide an electrical connection between the plug 104 and the power outlet 300.

In the example shown in FIG. 2, the adapter 200 is shown as having two sockets 202 arranged in a vertical configuration. In other examples, the adapter 200 can have alternative socket configurations such that the adapter 200 can have a single socket configuration, or multiple sockets arranged in vertical and/or horizontal configurations.

As shown in FIG. 1, the adapter 200 includes second antennas 204 that are embedded within the front surface 208 of the adapter 200. In some examples, the second antenna 204 is spaced or offset from the front surface 208 of the adapter 200 in a range from about 3 to about 4 cm. In some examples, the second antenna 204 is spaced or offset from the front surface 208 of the adapter 200 by less than 3 cm.

Each second antenna 204 has a shape that surrounds a socket 202 in the adapter 200. In some examples, the shape of each second antenna 204 is an ellipse (e.g., circle, oval, coil etc.) that surrounds a socket 202. In other examples, the shape of each second antenna 204 is a rectangle or square or other shape that can surround a socket 202. In some examples, a single second antenna 204 can surround multiple sockets 202. In some examples, it is contemplated that the second antenna 204 can be positioned in other areas of the socket 202.

In the example shown in FIG. 2, the adapter 200 includes two second antennas 204 (each second antenna 204 surrounds a socket 202). In other examples, the adapter 200 can have a single second antenna 204, or can have more than two second antennas 204 as may be needed and/or desired for a particular application.

In some examples, the first antenna 108 is a passive antenna that is part of a circuit that is not wired to a power source. As an example, the first antenna 108 can be a passive near-field communication (NFC) antenna such that the first antenna 108 is a "target" antenna meaning that the first antenna 108 remains in a sleep state unless powered by a radio-frequency (RF) field actively generated by another antenna. In certain examples, the first antenna 108 can have a simple form factor such as an unpowered tag or sticker (e.g., having a coil shape that surrounds the one or more prongs 106 of the plug 104). The coil shape of the first antenna 108 can reduce and/or eliminate the electromagnetic interference from one or more conductors that run in the power cord 102.

In some examples, each second antenna 204 is an active NFC antenna that can power the first antenna 108. Each second antenna 204 can be part of a circuit that actively generates an RF field using power drawn from the power outlet 300 when the adapter 200 is electrically connected to the power outlet 300. The RF field generated by each second antenna 204 can power the first antenna 108 when the first antenna 108 is spaced within a predetermined distance of a second antenna 204. In certain examples, the first antenna 108 is powered when spaced about 4 cm or less from a second antenna 204. This can occur when the one or more prongs 106 of the plug 104 are received in a socket 202 of the adapter 200 (and hence the first antenna 108 is proximate a second antenna 204). When the first antenna 108 is powered by a second antenna 204, the passive first antenna transfers the device ID to the second antenna 204.

In alternative examples, the first antenna 108 is an active NFC antenna such that the first antenna 108 is part of a separate circuit 112 that actively generates an RF field using the first antenna 108 so that the first antenna 108 and a second antenna 204 of the adapter 200 can wirelessly communicate with one another according to a peer-to-peer protocol. In such examples, the separate circuit 112 of the first antenna 108 can be located in the device 100 (e.g., not in the plug 104), and the separate circuit 112 can be connected to the first antenna 108 via a wire that runs in the power cord 102. The separate circuit 112 of the first antenna 108 can be powered by the power outlet 300 via the wire in the power cord 102 when the one or more prongs 106 are inserted in a socket 202 of the adapter 200, and the adapter 200 is electrically connected to the power outlet 300.

As shown in FIG. 2, the adapter 200 includes a controller 212 connected to a communication module 214 and to each second antenna 204. In certain examples, the controller 212 is a microprocessor that includes an internal memory. In some examples, the internal memory of the controller 212 can store data such as a power outlet ID that can be used to identify the power outlet 300 to which the adapter 200 is connected. In some examples, the internal memory of the controller 212 contains the data as read-only data. In some examples, the data stored on the internal memory of the controller 212 is rewriteable. In some examples, the internal memory of the controller 212 can store other data in addition to the power outlet ID.

In some examples, the controller 212 can receive and store the device ID from a second antenna 204, and can use the communication module 214 to wirelessly transfer the device ID and the power outlet ID to the network 20 (see FIG. 1). In some alternative examples, the controller 212 can transfer the power outlet ID and the device ID to the network 20 via a wired connection.

Referring back to FIG. 1, network 20 transmits the device ID and the power outlet ID to the computer server 30. In some examples, the network 20 transmits the device ID and the power outlet ID wirelessly to the computer server 30. In other examples, the network 20 transmits the device ID and the power outlet ID to the computer server 30 via a wired connection.

As shown in FIG. 1, the physical components (i.e., hardware) of the computer server 30 with which embodiments of the disclosure may be practiced are illustrated. In a basic configuration, the computer server 30 may include at least one processor 34, a memory 36, and a communication module 32. The communication module 32 can receive the device ID and the power outlet ID from the network 20. The processor 34 can use the device ID and the power outlet ID to determine the location of the device 100 within a room of the building. In some examples, the processor 34 can use a lookup table stored in the memory 36 that matches the power outlet ID to a particular room or a portion within a particular room of the building, such as a room or a portion of a room within the healthcare facility 2 shown in FIG. 1. Using the device ID, the processor 34 can determine that the device 100 is located within that particular room of the building. Also, the lookup table may have information that identifies a particular patient assigned to the device 100. Therefore, the processor 34 can identify the location of a patient within the healthcare facility 2 using the power outlet ID and the device ID.

Depending on the configuration and type of computer server, the memory 36 may comprise, but is not limited to, volatile storage (e.g., random access memory), non-volatile storage (e.g., read-only memory), flash memory, or any combination of such memories. The memory 36 may include an operating system and one or more program modules suitable for running software applications. The operating system, for example, may be suitable for controlling the operation of the computer server 30. Furthermore, embodiments of the disclosure may be practiced in conjunction with a graphics library, other operating systems, or any other application program and is not limited to any particular application or system. The computer server 30 may have additional features or functionality. For example, the computer server 30 may also include additional data storage devices (removable and/or non-removable) such as, for example, magnetic disks, optical disks, or tape.

The computer server 30 can include, or be connected to, a display 38 that displays the location of the device 100. In some examples, the display 38 can display the location of the device 100 as a room number. In other examples, the display 38 can display the location of the device 100 as a point within a map of the building.

Figure 4:
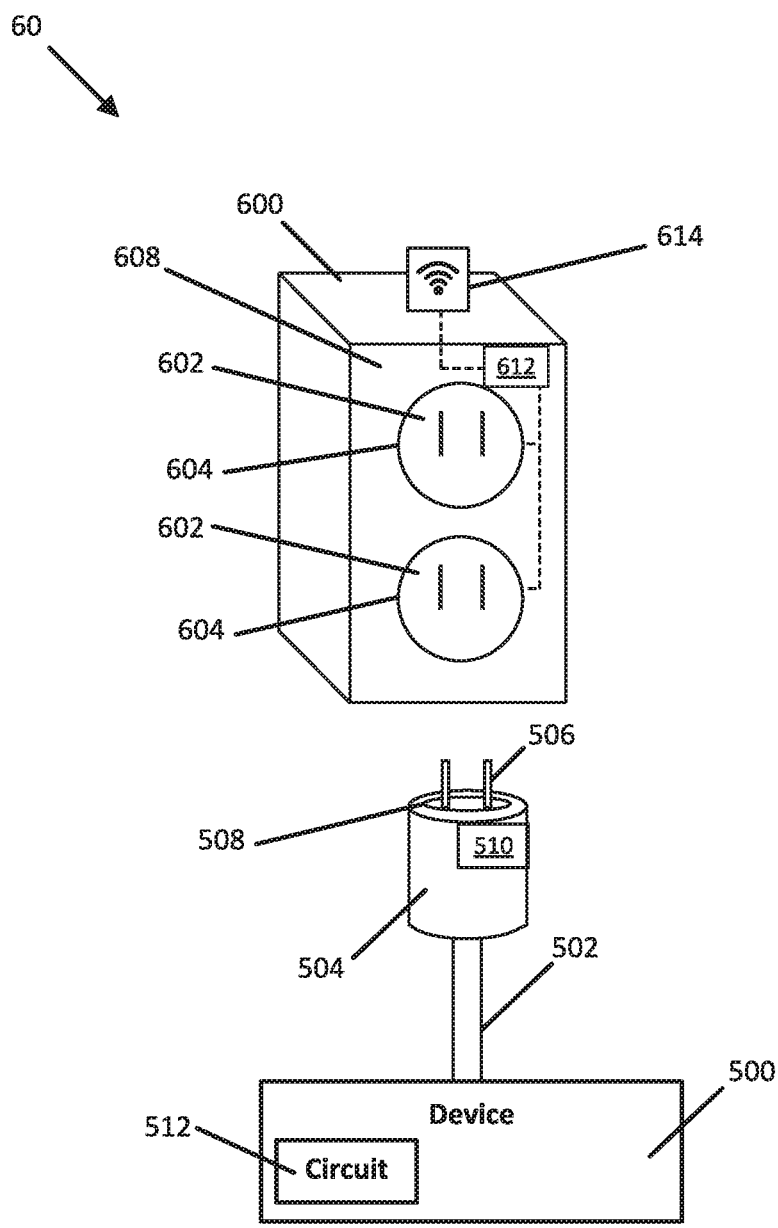
FIG. 4 is a schematic diagram of another system that can identify a location of a device.

FIG. 4 is a schematic diagram of an alternative system 60 that can identify a location of a device 500 within a room of a building. Like in the first example embodiment described above, the device 500 can be a hospital bed within a large building such as a hospital that can have multiple floors and rooms.

The device 500 includes a power cord 502 having at one end a plug 504 and one or more prongs 506 that extend from the plug 504. The one or more prongs 506 are configured to couple the plug 504 to a socket 602 of a power outlet 600. When coupled to the socket 602, the one or more prongs 506 draw electrical power from the power outlet 600 for powering the device 500. In the example shown, the device 500 is a hospital bed. The prongs 506 draw electrical power from the power outlet 600 for powering the hospital bed, including such features as height adjustment, entertainment options like television control, and/or emergency alert options like a call button that can be actuated by the patient to summon assistance from a caregiver.

The plug 504 carries a first antenna 508. The first antenna 508 has a shape that surrounds the one or more prongs 506 of the plug 504. In some examples, the shape of the first antenna 508 is an ellipse (e.g., circle, oval, coil etc.) that surrounds the one or more prongs 506. In other examples, the shape of the first antenna 508 is a rectangle or square or other shape that can surround the one or more prongs 506. In some examples, it is contemplated that the first antenna 508 can be positioned in other areas of the plug 504.

In some examples, the first antenna 508 is embedded in the plug 504 such that the first antenna 508 is spaced or offset from an exterior surface of the plug 504 in a range from about 3 to about 4 cm. In some examples, the first antenna 508 is embedded in the plug 504 such that the first antenna 508 is spaced or offset from an exterior surface of the plug 504 by less than 3 cm.

The plug 504 can have a memory 510 connected to the first antenna 508 and/or embedded within the first antenna 508. The memory 510 can store data such as a device ID that can be used to identify the device 500. In some examples, the memory 510 contains the data as read-only data. In some examples, the data stored on the memory 510 is rewriteable. In some examples, the memory 510 can store other data in addition to the device ID.

In the example shown in FIG. 4, the power outlet 600 includes a faceplate 608 that can replace a standard faceplate of the power outlet. The faceplate 608 of the power outlet 600 includes several features (described in more detail below) that can be used to identify the location of the device 500 when connected to the power outlet 600.

Figure 5:
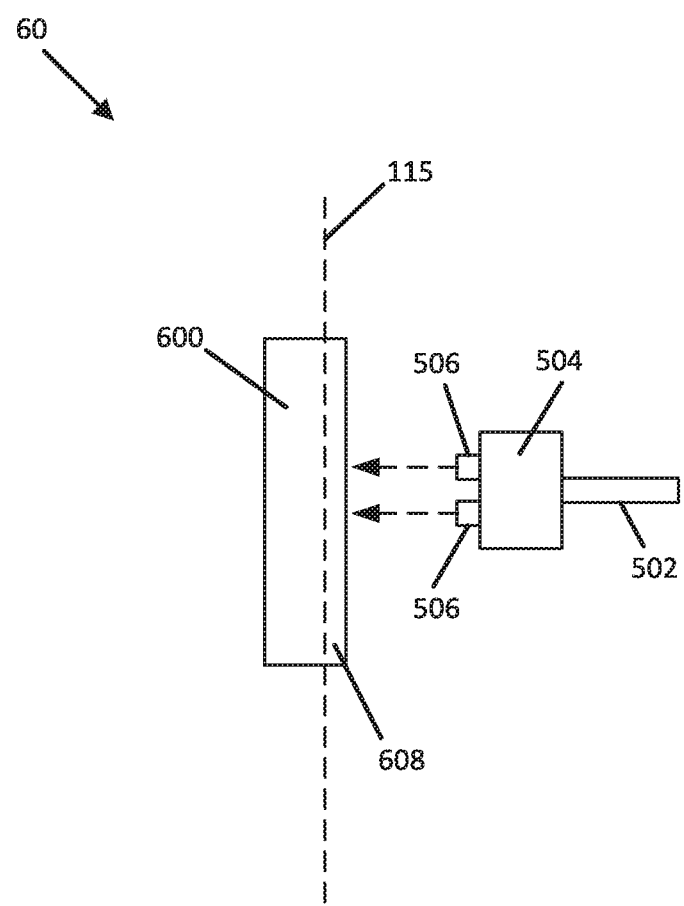
FIG. 5 is a side view showing an interface between a plug and a power outlet in the system of FIG. 4.

FIG. 5 is a side view showing an interface between the plug 504 and the power outlet 600. As shown in FIGS. 4 and 5, the one or more prongs 506 couple the plug 504 to a socket 602 of a power outlet 600 such that the plug 504 abuts and/or faces within close proximity the faceplate 608 of the power outlet 600. As shown in FIG. 5, the faceplate 608 is substantially parallel to a wall 115 of a room and is substantially flush with the wall 115.

As shown in the example of FIG. 4, the power outlet 600 has two sockets 602 arranged in a vertical configuration. In other examples, the power outlet 600 can have alternative socket configurations such that the power outlet 600 can have a single socket configuration, or multiple sockets arranged in vertical and/or horizontal configurations.

Figure 6:
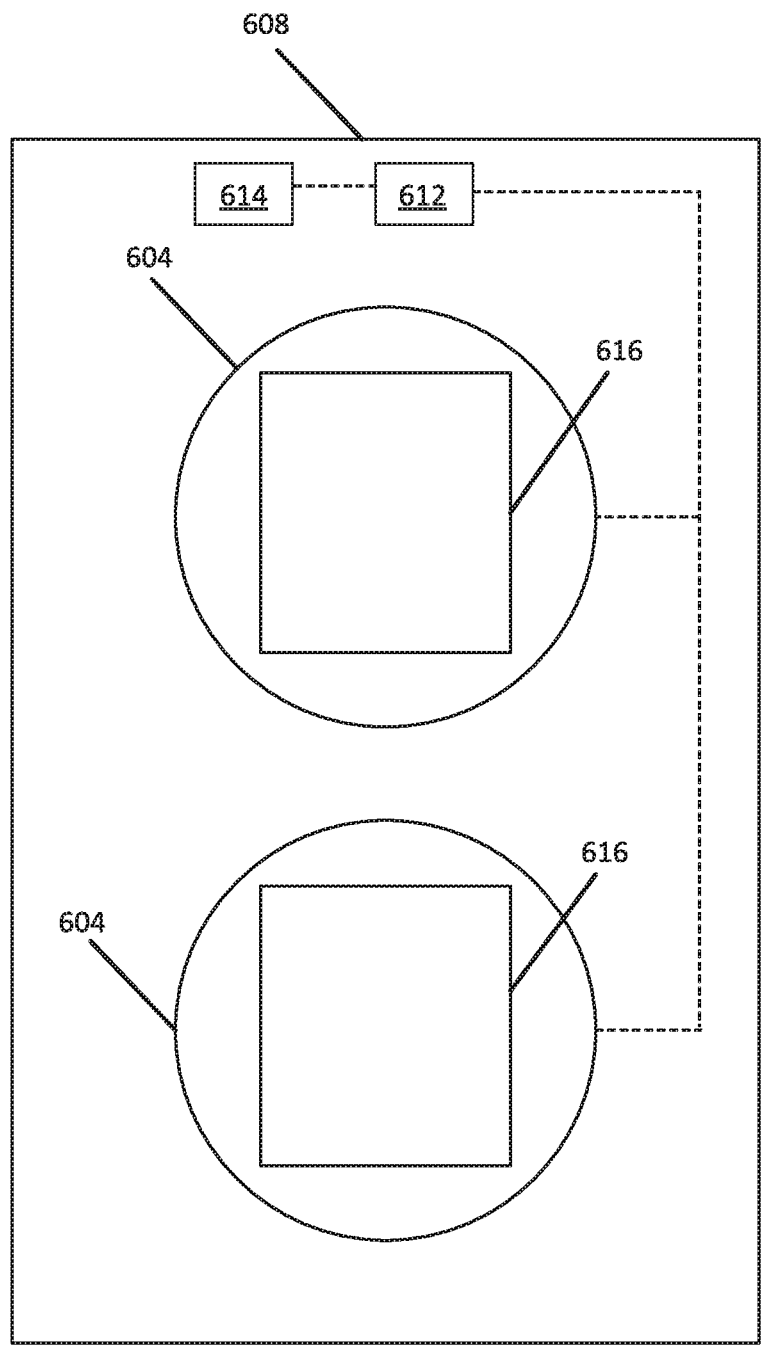
FIG. 6 is a rear view of a faceplate of the power outlet in the system of FIG. 4.

FIG. 6 is a rear view of the faceplate 608. As shown in FIG. 6, the faceplate 608 can include one or more openings 616 that surround the sockets 602 of the power outlet 600 when the faceplate 608 is mounted to the power outlet 600. The shape and configuration of the openings 616 in the faceplate 608 can be modified depending on the configuration of the sockets 602 in the power outlet 600. For example, faceplate 608 can have a single opening or multiple openings (e.g., two openings), and the openings of the faceplate 608 can be arranged in a vertical and/or horizontal configuration depending on the configuration of the sockets 602.

As shown in FIGS. 4 and 6, the faceplate 608 includes second antennas 604 embedded within a front surface of the faceplate 608. Each second antenna 604 has a shape that surrounds an opening 616 (and hence a socket 602 of the power outlet 600 when the faceplate 608 is mounted to the power outlet 600). In some examples, the shape of each second antenna 604 is an ellipse (e.g., circle, oval, coil etc.) that surrounds the one or more openings 616. In other examples, the shape of each second antenna 604 is a rectangle or square or other shape that can surround the one or more openings 616. In some examples, a single second antenna 604 can surround multiple openings 616. In some examples, it is contemplated that the second antenna 604 can be positioned in other areas of the faceplate 608.

In the example shown in FIGS. 4 and 6, the faceplate 608 includes two second antennas 604 (each second antenna 604 surrounding an opening 616). In other examples, the faceplate 608 can have a single second antenna 604, or can have more than two second antennas 604 as needed and/or desired for a particular application.

In some examples, the first antenna 508 is a passive near-field communication (NFC) antenna such that the first antenna 508 is a "target" antenna meaning that the first antenna 508 remains in a sleep state unless powered by a radio-frequency (RF) field actively generated by another antenna. In certain examples, the first antenna 508 can have a simple form factor such as an unpowered tag or sticker (e.g., having a coil shape that surrounds the one or more prongs 506 of the plug 504). The coil shape of the first antenna 508 can reduce and/or eliminate the electromagnetic interference from one or more conductors that run in the power cord 502.

In some examples, each second antenna 604 is an active NFC antenna that can power the first antenna 508. Each second antenna 604 can be part of a circuit that actively generates an RF field using power drawn from the power outlet 600. The RF field generated by each second antenna 604 can power the first antenna 508 when the first antenna 508 is spaced within a predetermined distance of a second antenna 604. In certain examples, the first antenna 508 is powered when spaced 4 cm or less from a second antenna 604. This can occur when the one or more prongs 506 of the plug 504 are received in a socket 602 of the power outlet 600 (and hence the first antenna 508 is proximate a second antenna 604). When the first antenna 508 is powered by a second antenna 604, the first antenna 508 transfers the device ID to the second antenna 604.

In alternative examples, the first antenna 508 is an active NFC antenna such that the first antenna 508 is part of a separate circuit 512 that actively generates an RF field using the first antenna 508 so that the first antenna 508 and a second antenna 604 of the power outlet 600 can wirelessly communicate with one another according to a peer-to-peer protocol. In such examples, the separate circuit 512 can be located in the device 500 (e.g., not in the plug 504), and the separate circuit 512 can be connected to the first antenna 508 via a wire that runs in the power cord 502. The separate circuit 512 of the first antenna 508 can be powered by the power outlet 600 via the wire in the power cord 502 when the one or more prongs 506 are inserted in a socket 602 of the power outlet 600.

As shown in FIGS. 4 and 6, the faceplate 608 includes a controller 612 connected to a communication module 614 and to each second antenna 604. In certain examples, the controller 612 is a microprocessor having an internal memory. In some examples, the internal memory of the controller 612 can store data such as a power outlet ID that can be used to identify the power outlet 600. In some examples, the internal memory of the controller 612 contains the data as read-only data. In some examples, the data stored on the internal memory of the controller 612 can be rewriteable. In some examples, the internal memory of the controller 612 can store other data in addition to the power outlet ID.

In some examples, the controller 612 can receive and store the device ID from a second antenna 604, and can use the communication module 614 to wirelessly transfer the device ID and the power outlet ID to the network 20 (see FIG. 1). In some alternative examples, the controller 612 can transfer the power outlet ID and the device ID to the network 20 via a wired connection.

As described above, the network 20 can transfer the device ID and the power outlet ID to the computer server 30. Thereafter, the computer server 30 can use the device ID and power outlet ID data to determine the location of the device 500 within a building, such as the healthcare facility 2 (see FIG. 1). For example, the computer server 30 can use a lookup table to determine the location of the device 500 using the device ID and the power outlet ID, and can also identify the location of a patient associated with the device 500 using the lookup table.

Figure 7:
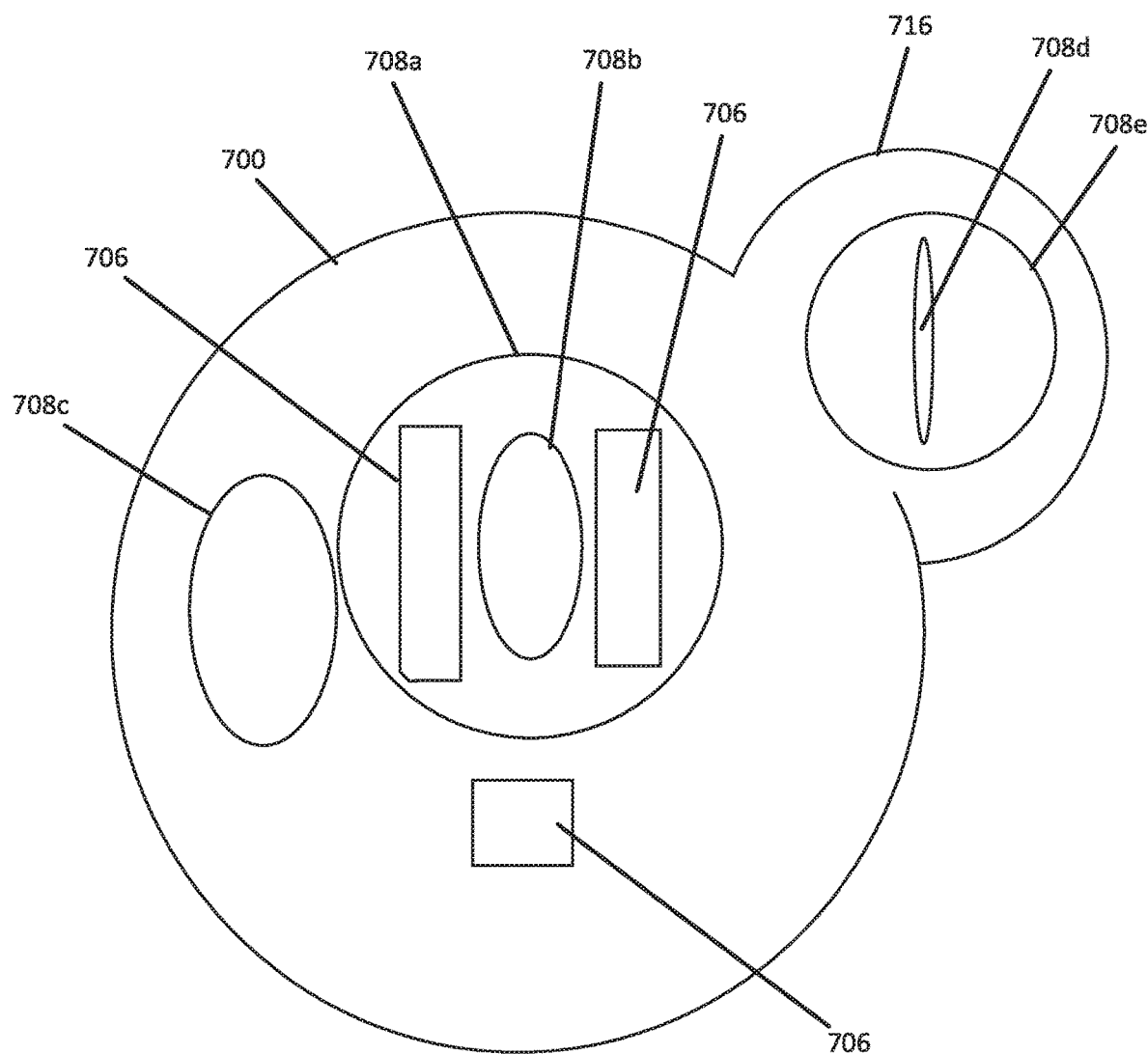
FIG. 7 is a front view of a plug showing alternative shapes and locations for an antenna carried by the plug.

FIG. 7 is a front view of a plug 700 for a medical device showing alternative shapes and locations for an antenna carried by the plug 700. These shapes and locations for the antenna can be implemented separately (i.e., a single antenna can be shaped and located in any of the positions shown) and/or multiple antenna can be provided on the plug 700.

As shown in FIG. 7, an antenna 708a has a coil shape and is located to surround one or more prongs 706 on the plug 700. The antenna 708a is similar to the first antenna 108 of the plug 104 in that the antenna 708a is positioned to surround prongs 706 of the plug 700.

Another alternative antenna 708b has a coil shape and is located between the prongs 706. In this example, the antenna 708b is completely bounded by the prongs 706 on at least two sides.

Another alternative antenna 708c has a coil shape located adjacent to the one or more prongs 706, but the antenna 708c does not surround the one or more prongs (unlike the antenna 708a) and is not between the one or more prongs 706 (unlike the antenna 708b).

In other examples, the antennas 708a, 708b, and 708c on the plug 700 can have shapes such as an ellipse, circle, oval, rectangle, square, and the like.

In view of the alternative shapes and locations of the antennas 708a, 708b, and 708c on the plug 700, a corresponding antenna (not shown) on a front surface of an adapter (such as the adapter 200 in FIGS. 2 and 3) or a faceplate of a power outlet (such as the power outlet 600 in FIGS. 4 and 5) can have a shape and location that corresponds to the shape and location of an antenna 708a, 708b, and 708c so that when the plug 700 is inserted into the adapter or power outlet, the antenna 708a, 708b, and 708c on the plug 700 aligns with the corresponding antenna.

Alternatively, the plug 700 can have a form factor that includes a structure 716 that projects laterally from the plug 700. As shown in FIG. 7, the structure 716 has an ear-like appearance. In this example, an antenna 708d is located in the structure 716. In yet another example, an antenna 708e having a coil shape is located in the structure 716. In other examples, the antennas 708d and 708e can have shapes such as an ellipse, circle, oval, rectangle, square, and the like. Also, a front surface of an adapter (such as the adapter 200 in FIGS. 2 and 3) or a faceplate of a power outlet (such as the power outlet 600 FIGS. 4 and 5) can have a corresponding ear-like structure (not shown) that includes a corresponding antenna such that when the plug 700 is inserted into the adapter or power outlet, the antenna 708d, 708e in the structure 716 aligns with the corresponding antenna of the adapter or power outlet.

In the examples shown, the antenna is incorporated into the plug of the medical device. In alternative embodiments, the antenna can be incorporated as part of an adapter into which the plug of the medical device is inserted. This adapter can include the unique identifier for the medical device, as well as prongs to be connected to a power outlet and the antenna to communicate therewith as described herein. Other configurations are possible.

Although the configurations described herein include a passive antenna on the plug side and an active reader antenna on the outlet side, the sides could be switched. In this alternative, a passive sticker or faceplate including the antenna can be applied on the wall outlet side or a pass-through adapter that has memory and is passive. The plug for the medical device can include the reader, and the processor, and memory. The wireless radio can be provided on the bedside to broadcast the identification information to an access point and/or a central computing system.

Figure 8:
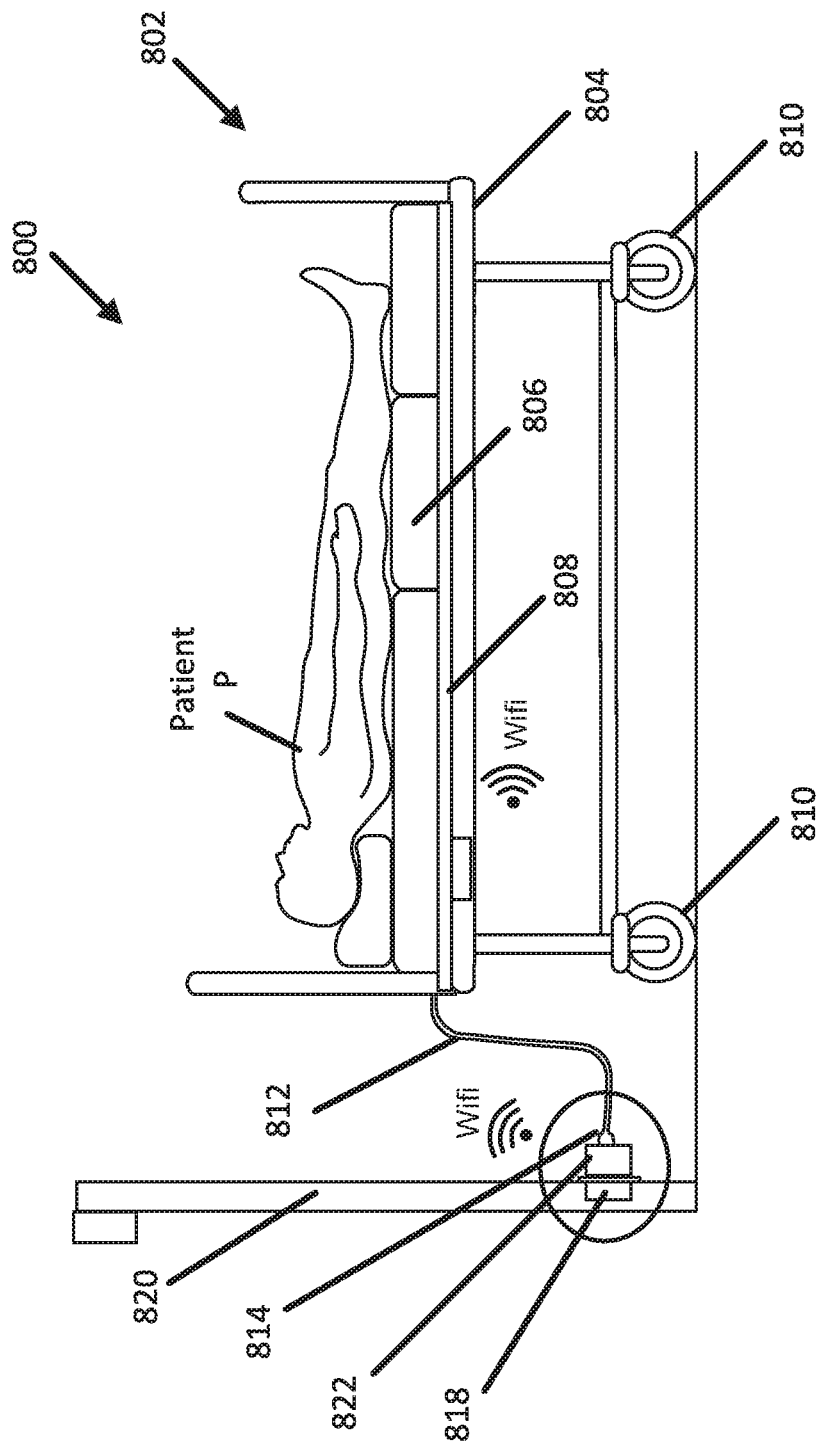
FIG. 8 illustrates a system for identifying the location of a device within a facility having multiple rooms.

FIG. 8 illustrates a system 800 that can identify the location of a device 802 within a facility having multiple rooms such as the healthcare facility illustrated in FIG. 1. While the device 802 is illustrated in FIG. 8 as a hospital bed that supports a patient P, the various concepts and features described herein can be incorporated into other types of devices including patient monitoring devices, medical diagnostic devices, patient lift devices, and the like.

The device 802 includes wheels 810 such that the device 802 is portable. For example, the device 802 can be wheeled from one room in the facility to another room in the facility. As described above, the system 800 can determine the location of the device 802 within the facility.

In some embodiments, the device 802 is configured to measure one or more physiological parameters of the patient P such as heart rate, respiratory rate, motion, weight, and the like. The one or more physiological parameters of the patient P can be used to identify early detection of patient deterioration, prevent falls, and prevent pressure ulcers.

In some embodiments, a secondary device 808 is attached to a frame 804 of the device 802 such that the secondary device 808 measures the one or more physiological parameters of the patent P. In the example illustrated in FIG. 8, the secondary device 808 is positioned under a mattress 806 of the device 802 to non-invasively measure the physiological parameters of the patent P. Alternatively, the secondary device 808 can be positioned elsewhere on the frame 804 of the device 802 to non-invasively measure the physiological parameters of the patent P.

As shown in FIG. 8, a power cord 812 is terminated by a plug 814. The plug 814 can have one or more prongs to couple the plug 814 to a power outlet 818 mounted to a wall 820 of the room where the device 802 is located within the facility. When coupled to the power outlet 818, the plug 814 and power cord 812 draw electrical power from the power outlet 818.

In one example embodiment, the power cord 812 and plug 814 belong to the device 802 such that the power cord 812 and plug 814 draw electrical power for powering the device 802. In the example shown, the device 802 is a hospital bed such that the electrical power drawn from the power outlet 818 can be used to power the hospital bed, including features such as height adjustment, entertainment options like television control, and/or emergency alert options like a call button that can be actuated by the patient to summon assistance from a caregiver.

In another example embodiment, the power cord 812 and plug 814 belong to the secondary device 808 that is associated with the device 802 such that the power cord 812 and plug 814 draw electrical power for powering the secondary device 808. In this example embodiment, the secondary device 808 is associated with the device 802. In the example shown, the secondary device 808 is a sensor placed under the mattress 806 of the device 802 such that the electrical power drawn from the power outlet 818 can be used to power the secondary device 808 for measuring heart rate, respiratory rate, motion, weight and the like.

An adapter 822 is installed onto the power outlet 818. The adapter 822 can be fixed to the power outlet 818 by one or more fasteners such as screws. Alternatively, the adapter 822 can be fixed to the wall surrounding the power outlet 818 by one or more fasteners such as screws. The adapter 822 is configured to plug into the power outlet 818, and provides an electrical connection between the power outlet 818 and the plug 814 when the adapter 822 is plugged into the power outlet 818 and the plug 814 is plugged into the adapter 822.

Figure 9:
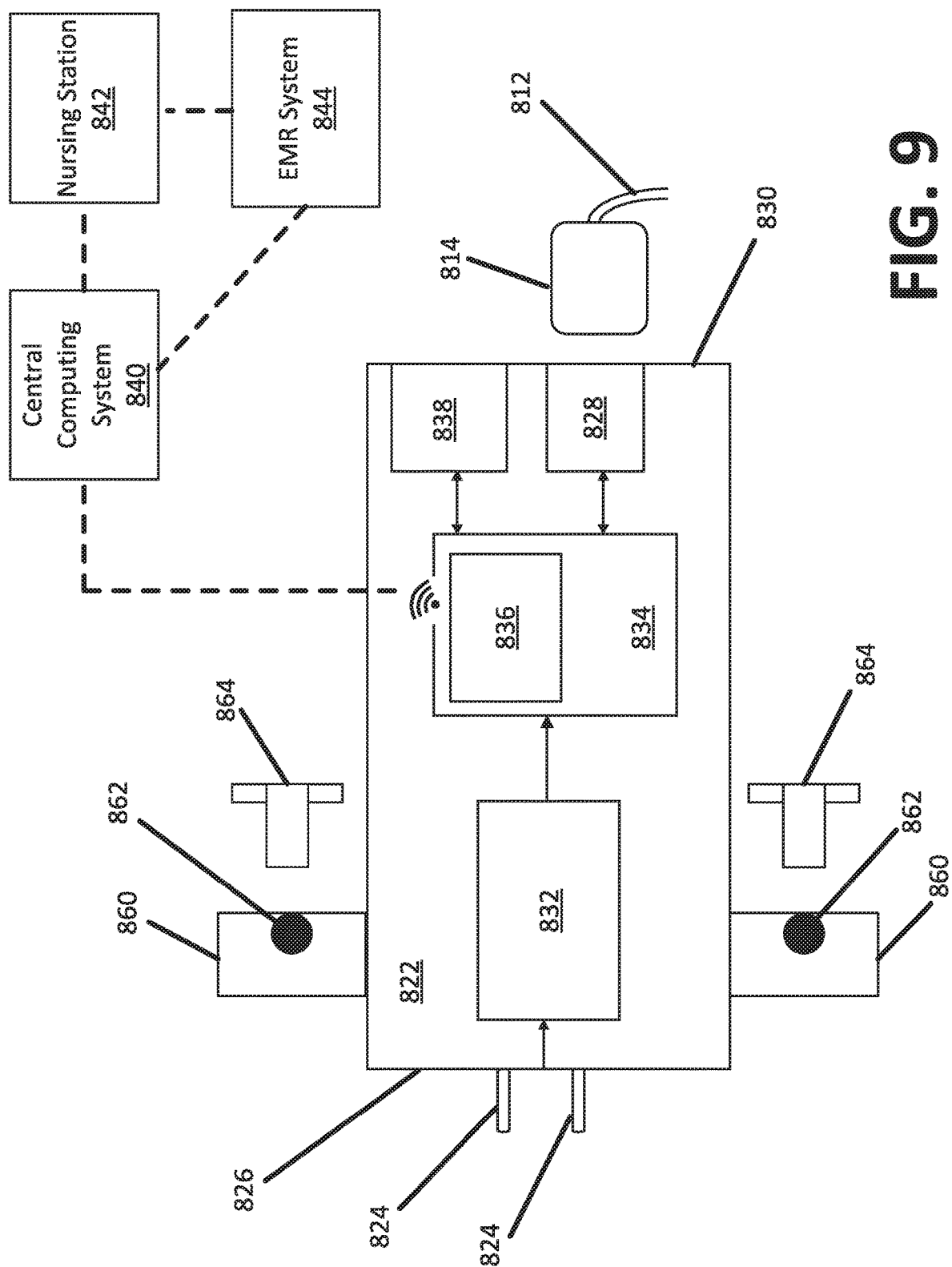
FIG. 9 is a schematic block diagram of an adapter used in the system of FIG. 8.

FIG. 9 is a schematic block diagram of the adapter 822. The adapter 822 includes one or more electrical couplings 824 on a rear surface 826 that are insertable into at least one socket of the power outlet 818 to plug the adapter 822 into the power outlet 818. When plugged into the power outlet 818, the adapter 822 is electrically connected to the power outlet 818. In the example illustrated in FIG. 9, the electrical couplings 824 are illustrated as prongs that extend from the rear surface 826. The electrical couplings 824 can have a variety of shapes and configurations to electrically connect the adapter 822 to the power outlet 818.

The adapter 822 includes one or more flanges 860 each having a bore 862 configured to receive a fastener 864 such as a screw. The adapter 822 can be fixed to a power outlet by inserting the fasteners 864 through the bores 862 and into corresponding bores on the power outlet. Alternatively, the adapter 822 can be fixed to the wall surrounding the power outlet 818 by inserting the fasteners 864 through the bores 862 and into the wall.

As shown in FIG. 9, the adapter 822 includes an electrical converter 832 operatively connected to an electronic board 834 having a communication transceiver 836. The electrical converter 832 converts an alternating current (AC) from the power outlet 818 to a direct current (DC) that can be used by the electronic board 834. As an illustrative example, the electrical converter 832 can convert 110/220 VAC from the power outlet 818 into 5 VDC.

The electronic board 834 can accept data as input, process the data according to instructions stored in a memory of the electronic board 834, and provide results as an output. The electronic board 834 stores a unique adapter identifier (i.e., "adapter ID") in its memory.

A touch screen 838 is operatively connected to the electronic board 834. The touch screen 838 is configured to display a graphical user interface for use by an installer during installation of the adapter 822 onto the power outlet 818, and to receive information from the installer identifying the location of the power outlet 818 within the facility. The information received from the touch screen 838 can be stored in a memory of the electronic board 834.

Figure 10:
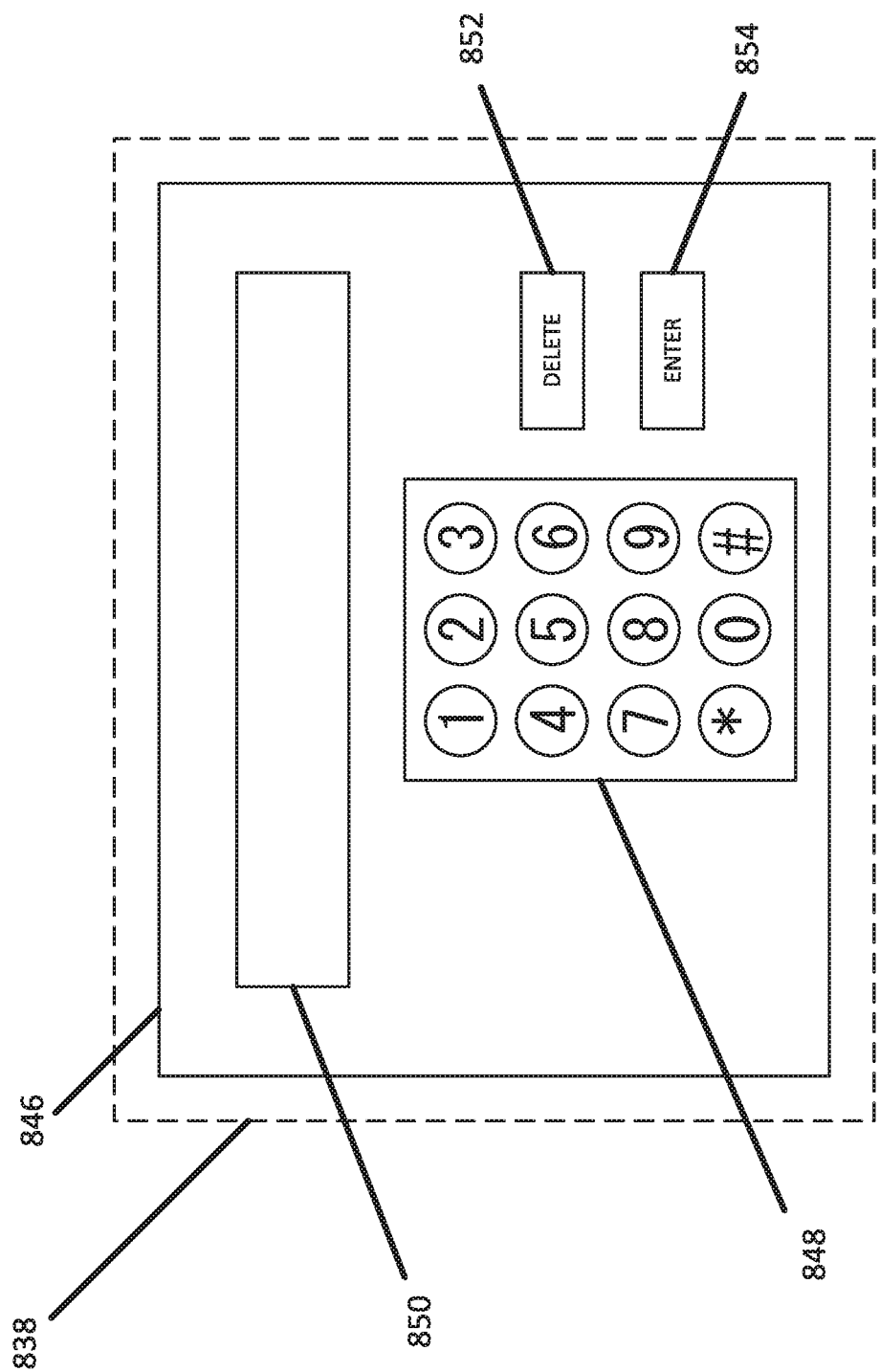
FIG. 10 illustrates an example graphical user interface on a touch screen of the adapter.

FIG. 10 illustrates an example graphical user interface 846 for the touch screen 838 of the adapter 822. In this illustrative example, the graphical user interface 846 includes a keyboard 848 that can be used by an installer of the adapter 822 to type one or more digits representing information where the power outlet 818, onto which the adapter 822 is installed, is located within the facility. The typed digits can be displayed in a display field 850 for review by the installer.

In some examples, a delete button 852 can be used by the installer to delete one or more typed digits displayed in the display field 850. An enter button 854 can be used by the installer to enter the typed digits displayed in the display field 850 when the information is correct to the satisfaction of the installer. While a numerical keyboard 848 is shown, a variety of keyboards, including QWERTY keyboards, can be displayed on the graphical user interface 846 for use by the installer to enter the information identifying the location of the power outlet 818.

In alternative embodiments, information such as the room number where the adapter 822 is installed can be stored in the memory of the electronic board 834 by using a mobile device such as a smartphone equipped with an application that can communicate the room number to the adapter 822 such that the touch screen 838 can be eliminated from the adapter 822. In such embodiments, the communication transceiver 836 can wirelessly receive the room number from the mobile device during installation of the adapter 822 onto the power outlet 818.

In some examples, a subsection room number identifying a portion of a particular room within the facility is entered into the adapter 822 using the touch screen 838 or mobile device to identify the particular portion of the room where power outlet 818 is mounted. In this example, the portion of the room may be relevant when there are multiple power outlets 818 in each room and multiple patients share a room within the facility such as in a hospital having multi-occupancy rooms. The room number and subsection room number will be collectively referred to herein as an power outlet ID that identifies a location of the power outlet within the facility.

An association between the adapter ID and power outlet ID is generated. In some examples, the association is transmitted from the adapter 822 to a central computing system 840 for storage in a lookup table in the central computing system 840. Advantageously, the association between the adapter ID and the power outlet ID is generated only once during installation of the adapter 822 and does not need to be repeated after installation.

At least one connector port 828 is included on a front surface 830 of the adapter 822. The connector port 828 is configured to receive the plug 814 to electrically connect the device 802 or secondary device 808 to the adapter 822. Accordingly, an electrical circuit between the power outlet 818 and the device 802 or secondary device 808 is established when the plug 814 is plugged into the at least one connector port 828 and the electrical couplings 824 of the adapter 822 are plugged into the power outlet 818. While only one connector port 828 is shown in FIG. 9, the adapter 822 can include a plurality of connector ports 828.

In some examples, in addition to supplying electrical power, the electrical circuit transfers data between the device 802 or secondary device 808 and the adapter 822. For example, the electrical circuit can transfer a unique device identifier (i.e., "device ID") from the device 802 or secondary device 808 to the adapter 822 for storage in the memory of the electronic board 834 when the device 802 or secondary device 808 are plugged into the adapter 822.

The device ID of the secondary device 808 can be associated with the device 802. Thus, in instances where the secondary device 808 is plugged into the adapter 822, the device ID of the secondary device 808 can be used to determine that the device 802 is located proximate to the adapter 822. In some examples, the association between the device ID of the secondary device 808 with the device 802 is stored in a lookup table in the central computing system 840.

In some examples, the transfer of the device ID from the device 802 or secondary device 808 to the adapter 822 is established through a USB connection. Alternatively, the transfer of the device ID from the device 802 or secondary device 808 to the adapter 822 can be established through a Controller Area Network (CAN) connection. In other examples, the transfer of the device ID from the device 802 or secondary device 808 to the adapter 822 can be done wirelessly such as through Wi-Fi or Bluetooth. In further examples, the transfer of the device ID from the device 802 or secondary device 808 to the adapter 822 can be done through one or more of the methods described above such as through a combination of near-field communication (NFC) antennas attached to the plug 814 and adapter 822, respectively.

The communication transceiver 836 is configured to wirelessly transmit the device ID together with the power outlet ID to the central computing system 840. As shown in FIG. 9, the central computing system 840 is located remotely from the adapter 822. By transmitting the device ID together with the power outlet ID, the location of the device 802 or secondary device 808 within the facility can be determined by the central computing system 840.

Advantageously, the system 800 eliminates the need for a clinician to manually update the location of the device 802 or secondary device 808 each time the device 802 or secondary device 808 are moved within the facility. Further, the system 800 eliminates the need for a real-time location system (RTLS) to track the location of the device 802 or secondary device 808 within the facility such that the cost and complexity associated with RTLS are eliminated.

In some alternative embodiments, the device 802 or secondary device 808 transmit the measured physiological parameters to the adapter 822 via the plug 814 and power cord 812. In such embodiments, the communication transceiver 836 can be configured to transmit the measured physiological parameters from the adapter 822 to the central computing system 840.

In some examples, the central computing system 840 transmits the location of the device 802 or secondary device 808 to a nursing station 842. This enables a clinician at the nursing station 842 to enter the measured parameters from the device 802 or secondary device 808 into an electronic medical record associated with the patient P in an EMR system 844. By knowing the location of the device 802 or secondary device 808, the measured parameters from the device 802 or secondary device 808 can be confirmed as belonging to the patient P for storage in the electronic medical record of the patient P without requiring a real-time location system (RTLS).

In some further embodiments, the central computing system 840 stores the measured parameters into the EMR system 844 directly without requiring a clinician at the nursing station 842 to enter the measured parameters into the EMR system 844. Advantageously, this can further reduce errors by automating the process of saving the measured parameters from the device 802 or secondary device 808 into the correct electronic medical record in the EMR system 844.

Figure 11:
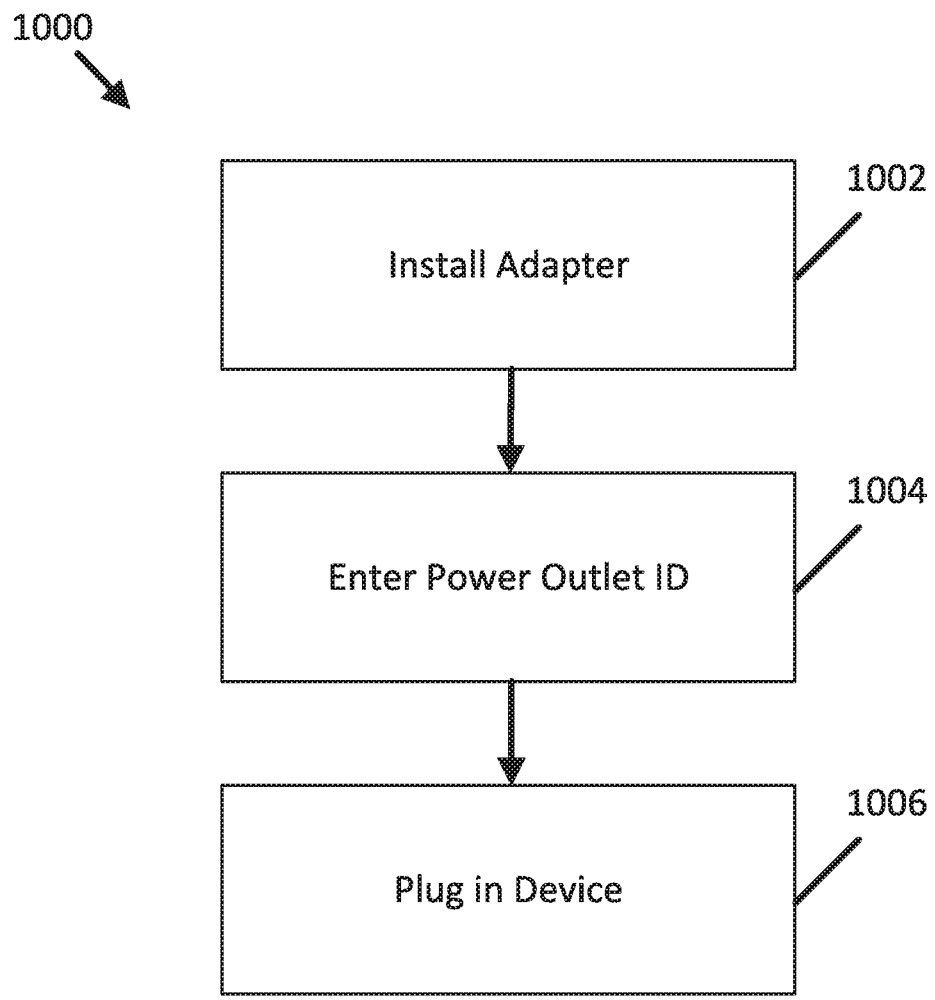
FIG. 11 illustrates a method for determining a location of a device within a facility.

FIG. 11 illustrates a method 1000 for determining a location of a device within a facility having multiple rooms. The method 1000 includes an operation 1002 installing an adapter, an operation 1004 of entering a power outlet ID, and an operation 1006 of plugging in a device.

With respect to operation 1002, the adapter is installed onto a power outlet mounted to a wall such as shown in FIG. 8. In some examples, adapter is fixed to the power outlet by one or more fasteners such as screws. Alternatively, the adapter is fixed to the wall surrounding the power outlet by one or more fasteners such as screws. During installation, the adapter is plugged into the power outlet providing an electrical connection between the power outlet and adapter.

With respect to operation 1004, the power outlet ID identifies the location of the power outlet within the facility. The adapter can include a touch screen that is used to type and enter the power outlet ID into a memory of the adapter. Alternatively, the power outlet ID can be entered into a memory of the adapter using a mobile device equipped with an application that can wirelessly transfer the power outlet ID to a communication transceiver of the adapter.

With respect to operation 1006, a device is plugged into the adapter. The device can include a power cord terminated by a plug configured for being plugged into the adapter. In some examples, the device is a medical device such as a hospital bed, patient monitoring device, medical diagnostic device, patient lift devices, and the like. When the device is plugged into the adapter, the device transfers a device ID to the adapter. The device ID together with the power outlet ID determine the location of the device within the facility.

Figure 12:
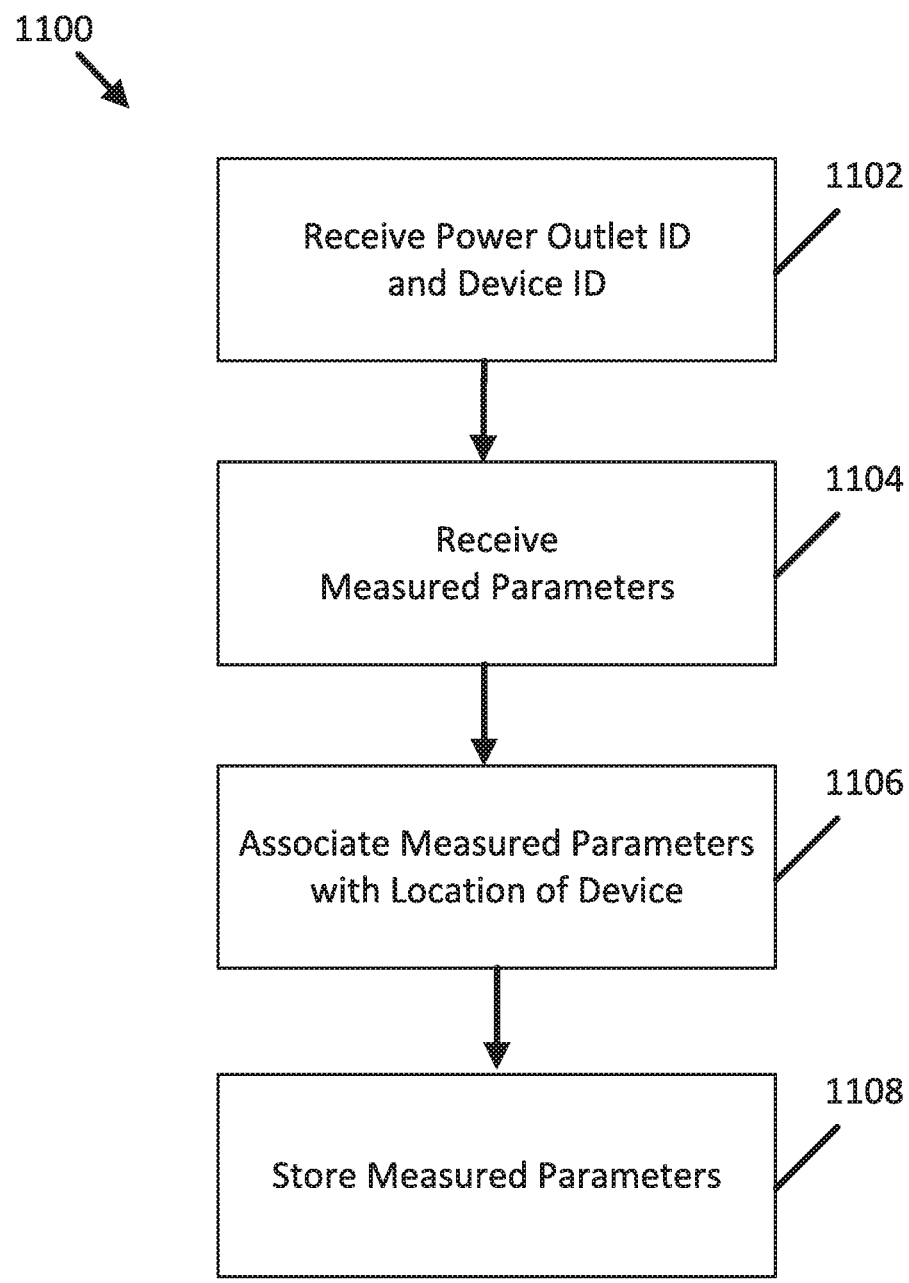
FIG. 12 illustrates a method for automatically saving measured parameters based on a location of a device within a facility having multiple rooms.

FIG. 12 illustrates a method 1100 for automatically saving measured parameters based on a location of a device within a facility having multiple rooms. The method 1100 includes an operation 1102 of receiving a power outlet ID and device ID, an operation 1104 of receiving the measured parameters, an operation 1106 of associating the measured parameters with the location of the device in the facility, and an operation 1108 of storing the measured parameters.

With respect to operation 1102, the power outlet ID and device ID are received from an adapter installed onto a power outlet within the facility. The power outlet ID is entered into the adapter during installation of the adapter onto the power outlet. The power outlet ID identifies the location of the power outlet within the facility. The device ID identifies a device plugged into the power outlet. The device ID together with the power outlet ID is received from the adapter to determine the location of the device within the facility.

With respect to operation 1104, the measured parameters are received from the device. In some examples, the measured parameters are received directly from the device via wireless communication. In other examples, the measured parameters are transmitted from the device to the adapter such that the measured parameters are received from the adapter via wireless communication. In some examples, the device is a medical device that is configured to measure one or more physiological parameters such as heart rate, respiratory rate, motion, and weight of a patient admitted to the facility. The one or more physiological parameters can be used to identify early detection of patient deterioration, prevent falls, and prevent pressure ulcers.

With respect to operation 1106, the measured parameters are associated with the location of the device in the facility. In examples where the device is a medical device such as a hospital bed or a sensor fixed to a hospital bed, the location of the device corresponds to the location of a patient admitted to the facility. The location of the patient can be used to confirm that the measured parameters are from the correct patient and not from another patient without requiring use of a real-time location system (RTLS).

With respect to operation 1108, the measured parameters are stored. In examples where the device is a medical device such as a hospital bed or a sensor fixed to a hospital bed, the measured parameters can be stored in an electronic medical record of a patient, the location of the patient having been identified by the determining the location of the device.

The various embodiments described above are provided by way of illustration only and should not be construed to limiting. Various modifications and changes that may be made to the embodiments described above without departing from the true spirit and scope of the disclosure.

What is claimed is:

1. An adapter for a power outlet, the adapter comprising:
   at least one connector port on a front surface, the connector port configured to receive a plug to electrically connect a device to the adapter;
   electrical couplings on a rear surface that are insertable into at least one socket of the power outlet to plug the adapter into the power outlet;
   an electronic board configured to receive a device ID from the device when plugged into the connector port and an outlet ID identifying a location of the power outlet; and
   a communication transceiver that transmits the device ID and the outlet ID from the electronic board to a central computing system, wherein the communication transceiver wirelessly receives the outlet ID from a mobile device during installation of the adapter to the power outlet.

2. The adapter of claim 1, wherein the communication transceiver wirelessly transmits the device ID and the outlet ID to the central computing system.

3. The adapter of claim 1, further comprising an electrical converter operatively connected to the electronic board and configured to convert an alternating current from the power outlet to a direct current usable by the electronic board.

4. The adapter of claim 1, wherein the adapter is configured for fixation to the power outlet or to a wall surrounding the power outlet by one or more fasteners.

5. The adapter of claim 1, further comprising an antenna on the front surface that is configured to receive the device ID from a corresponding antenna on the plug.

6. A method for determining a location of a device within a facility, the method comprising:
   installing an adapter onto a power outlet;
   entering a power outlet ID into the adapter, the power outlet ID identifying a location of the power outlet within the facility, wherein entering the power outlet ID into the adapter includes using a touch screen of the adapter to type and enter the power outlet ID; and
   plugging a device into the adapter.

7. The method of claim 6, further comprising transferring a device ID to the adapter when the device is plugged into the adapter, the transfer of the device ID from the device to the adapter established through USB, CAN, Wi-Fi, Bluetooth, or NFC connections.

8. The method of claim 7, wherein the adapter wirelessly transmits the device ID and the power outlet ID to a central computing system.

9. A method for automatically saving measured parameters comprising:
   receiving a power outlet ID through a touch screen of an adapter, the touch screen allowing for input of the power outlet ID;
   receiving a device ID associated with a device plugged into the power outlet, the power outlet ID together with the device ID determining the location of the device in the facility;
   receiving the measured parameters from the device;
   associating the measured parameters with the location of the device in the facility; and
   storing the measured parameters.

10. The method of claim 9, wherein the location of the device corresponds to a location of a patient in the facility, and the location of the patient being used to confirm that the measured parameters are from the patient without requiring use of a real-time location system.

11. The method of claim 9, wherein the device is positioned under a mattress of a hospital bed to non-invasively measure one or more physiological parameters of a patient.

12. The method of claim 11, wherein storing the measured parameters includes storing physiological parameters into an electronic medical record.

13. The method of claim 12, wherein the physiological parameters include heart rate, respiratory rate, weight, and motion of the patient.

14. An adapter for a power outlet, the adapter comprising:
   at least one connector port on a front surface, the connector port configured to receive a plug to electrically connect a device to the adapter;
   electrical couplings on a rear surface that are insertable into at least one socket of the power outlet to plug the adapter into the power outlet;
   an electronic board configured to receive a device ID from the device when plugged into the connector port and an outlet ID identifying a location of the power outlet;
   a communication transceiver that transmits the device ID and the outlet ID from the electronic board to a central computing system; and
   a touch screen configured to receive the outlet ID during installation of the adapter to the power outlet.

15. The adapter of claim 14, wherein the touch screen displays a graphical user interface having a keyboard to type the outlet ID.

16. The adapter of claim 15, wherein the graphical user interface further includes a display field for displaying the typed outlet ID on the adapter.

17. The adapter of claim 16, wherein the graphical user interface further includes a delete button to delete one or more typed digits displayed in the display field, and an enter button to enter the typed digits displayed in the display field.

* * * * *